United States Patent
Shibata

(10) Patent No.: US 8,676,532 B2
(45) Date of Patent: Mar. 18, 2014

(54) FALL DETECTION DEVICE, MAGNETIC DISK DRIVE, AND PORTABLE ELECTRONIC APPARATUS

(75) Inventor: Akihiko Shibata, Kanagawa-ken (JP)

(73) Assignee: Murata Manufacturing Co., Ltd., Kyoto-Fu (JP)

(*) Notice: Subject to any disclaimer, the term of this patent is extended or adjusted under 35 U.S.C. 154(b) by 5 days.

(21) Appl. No.: 12/727,795

(22) Filed: Mar. 19, 2010

(65) Prior Publication Data

US 2010/0172052 A1 Jul. 8, 2010

Related U.S. Application Data

(63) Continuation of application No. PCT/JP2008/065835, filed on Sep. 3, 2008.

(30) Foreign Application Priority Data

Sep. 21, 2007 (JP) ................. 2007-244737

(51) Int. Cl.
 *G01P 15/18* (2013.01)
 *G01P 15/08* (2006.01)
 *A61B 5/11* (2006.01)

(52) U.S. Cl.
 CPC ............ *G01P 15/18* (2013.01); *G01P 15/0891* (2013.01); *A61B 2562/0219* (2013.01); *A61B 5/1117* (2013.01)
 USPC .............. 702/141; 702/41; 702/152; 702/169

(58) Field of Classification Search
 CPC ................ G01P 15/18; G01P 15/0891; A61B 2562/0219; A61B 5/0002; A61B 5/1117
 USPC ..................... 702/41, 141, 152, 169
 See application file for complete search history.

(56) References Cited

U.S. PATENT DOCUMENTS

| 6,697,882 B1* | 2/2004 | Matsui .................. 710/6 |
| 2006/0116848 A1* | 6/2006 | Clifford et al. ............ 702/141 |

(Continued)

FOREIGN PATENT DOCUMENTS

| JP | 2000-241442 A | 9/2000 |
| JP | 2005-147899 A | 6/2005 |

(Continued)

OTHER PUBLICATIONS

Japanese Office Action "Notification of Reasons for Rejection" dated Jan. 17, 2012; Japanese Patent Application No. 2009-533101 with translation.

(Continued)

*Primary Examiner* — Sujoy Kundu
*Assistant Examiner* — Paul D Lee
(74) *Attorney, Agent, or Firm* — Studebaker & Brackett PC

(57) ABSTRACT

A fall detection device that is allowed to reduce the processing load put when making a determination using software, to reliably determine the start of a fall, and to make a fall prediction as necessary, and a magnetic disk drive and a portable electronic apparatus that each include the fall detection device are configured. Accelerations are obtained in three orthogonal axis directions ($a_x$, $a_y$, $a_z$), and an evaluation value is obtained with respect to each of the accelerations ($a_x$, $a_y$, $a_z$) on the basis of an evaluation function, by which an evaluation value is increased as the difference increases between accelerations ($a_{x0}$, $a_{y0}$, $a_{z0}$) at a steady time and accelerations ($a_x$, $a_y$, $a_z$) at a fall determination time, and whether a fall has started is determined on the basis of whether this evaluation value exceeds a predetermined value.

17 Claims, 16 Drawing Sheets

(56) References Cited

U.S. PATENT DOCUMENTS

| | | | |
|---|---|---|---|
| 2006/0152842 A1* | 7/2006 | Pasolini et al. | 360/75 |
| 2006/0236761 A1* | 10/2006 | Inoue et al. | 73/510 |
| 2006/0268447 A1* | 11/2006 | Liao et al. | 360/75 |
| 2007/0067139 A1* | 3/2007 | Kobayashi et al. | 702/150 |
| 2007/0086108 A1* | 4/2007 | Kuroki et al. | 360/75 |
| 2007/0121236 A1* | 5/2007 | Matsumoto | 360/60 |
| 2008/0001607 A1* | 1/2008 | Horiguchi et al. | 324/600 |
| 2008/0215970 A1* | 9/2008 | Tsuji et al. | 715/702 |
| 2009/0021858 A1* | 1/2009 | Fu et al. | 360/99.01 |
| 2009/0031803 A1* | 2/2009 | Noda et al. | 73/488 |
| 2010/0010771 A1* | 1/2010 | Ikkink et al. | 702/141 |

FOREIGN PATENT DOCUMENTS

| | | |
|---|---|---|
| JP | 2007-095182 A | 4/2007 |
| JP | 2007-101406 A | 4/2007 |
| JP | 2007-192826 A | 8/2007 |
| WO | 2006/061950 A1 | 6/2006 |

OTHER PUBLICATIONS

International Search Report; PCT/JP2008/065835; Dec. 9, 2008.
Written Opinion of the International Searching Authority; PCT/JP2008/065835; Dec. 9, 2008.

* cited by examiner

FALL DETECTION DEVICE, MAGNETIC DISK DRIVE, AND PORTABLE ELECTRONIC APPARATUS

CROSS REFERENCE TO RELATED APPLICATIONS

The present application is a continuation of International Application No. PCT/JP2008/065835, filed Sep. 3, 2008, which claims priority to Japanese Patent Application No. JP 2007-244737, filed Sep. 21, 2007, the entire contents of each of these applications being incorporated herein by reference in their entirety.

BACKGROUND

1. Field of the Invention

The invention relates to a fall detection device that detects whether an apparatus is placed in a fall state, on the basis of acceleration, and to a magnetic disk drive and a portable electronic apparatus that each include the fall detection device.

2. Description of the Related Art

Japanese Unexamined Patent Application Publication No. 2005-147899 (hereinafter, "the '899 application") and Japanese Patent Publication No. 3441668 (hereinafter, "the '668 application") describe apparatuses that detect whether an apparatus is placed in a fall state. FIG. 1 shows a configuration of a device according to the '899 application. This fall detection device includes an acceleration sensor 10, a differential circuit 42 that differentiates an acceleration detection signal outputted from the acceleration sensor 10 so as to output a differential signal, a first comparator 44 that determines whether the differential signal has reached a first predetermined threshold, a second comparator 46 that determines whether the differential signal has reached a second threshold higher than the first threshold, a voltage detector 50, and a processing circuit 48.

Suppose that the signal outputted from the acceleration sensor 10 has reached a predetermined setting value and is kept for a given time. In this case, when the differential signal reaches the first threshold, the fall detection device shown in FIG. 1 determines that the device is placed in a first processing state. When the differential signal reaches the second threshold, the fall detection device determines that the device is placed in a second processing state. Thus, for example, if a magnetic head of the hard disk drive is performing a recording operation when the fall detection device is placed in the first processing state, the fall detection device controls a safety operation such as suspending of the recording operation. If the fall detection device determines that the device is placed in the second processing state, it performs control, for example, so that the hard disk drive is put into a safer state.

A fall detection device according to the '668 application includes an acceleration sensor and a fall determination processing section and is configured to use both an acceleration and a differential value of the acceleration in order to determine whether the device is placed in a fall state.

However, the fall detection device according to the '899 application must use two thresholds simultaneously to determine a fall. This complicates a determination process. For this reason, particularly when a determination is made using software, problems occur, such as increasing the calculation load put on the CPU is increased and increasing the processing time.

Also, while the '899 application can determine a state in which the device is placed in a fall state and a state in which a shock has been given to the device, the '899 application has a problem that it is not possible to detect (predict a fall) a state in which the start of a fall is suspected. Therefore, it is not possible to perform a process of corresponding to the fall early.

Also, in the '899 application, an acceleration is used to make a determination. However, it is necessary to perform an offset adjustment on the acceleration sensor because an acceleration detection value obtained by the acceleration sensor includes an offset.

Also, for example, in a case where the device falls while it rotates, an acceleration caused by centrifugal force thereof is added. Therefore, the acceleration detection value is susceptible to the centrifugal force caused by the rotation. Thus, if the device falls while it rotates, a proper determination may not be made.

The fall detection device according to the '668 application also uses an acceleration and a differential value of the acceleration simultaneously. This complicates a determination process and causes the same problem as the problem with the '899 application. Also, a fall prediction cannot be made.

Also, variations in differential value of an acceleration is caused not only by the start of a fall but also by a simple, small shock (hereafter referred to as a "simple shock") given when the device is handled. Therefore, it may be difficult to determine whether the device has actually started to fall or has been given a simple shock, on the basis of only variations in differential value of an acceleration.

SUMMARY

To overcome the problems described above, embodiments in accordance with the invention provide a fall detection device that is allowed to resolve the above-mentioned problems and thus reduce the processing load put when making a determination using software, is allowed to reliably determine the start of a fall, and is allowed to make a fall prediction as necessary, and a magnetic disk drive and a portable electronic apparatus that each include the fall detection device.

A fall detection device according to an embodiment is configured to detect a fall on the basis of a signal outputted from an acceleration sensor. The device includes acceleration detection means that obtains accelerations in three orthogonal axis directions; and fall start determination means that obtains an evaluation value with respect to each of the accelerations in the three axis directions detected by the acceleration detection means on the basis of an evaluation function, by which an evaluation value is increased as a difference between an acceleration at a steady time and an acceleration at a fall determination time is increased, and determines the start of a fall on the basis of whether the evaluation value exceeds a predetermined threshold.

According to this configuration, it is possible to properly determine, for example, whether variations in the absolute value of a differential value of an acceleration or variations in differential value of the absolute value of an acceleration are due to the start of a fall or due to a simple shock.

In another aspect, if a value of the evaluation function is represented by A, accelerations in the three axis directions at the steady time are represented by $(a_{x0}, a_{y0}, a_{z0})$ and accelerations at the fall determination time are represented by $(a_x, a_y, a_z)$, relations among the A, the $(a_{x0}, a_{y0}, a_{z0})$, and the $(a_x, a_y, a_z)$ are represented by the following equation:

$$A = \sqrt{\{(a_x - a_{x0})^2 + (a_y - a_{y0})^2 + (a_z - a_{z0})^2\}}.$$

Thus, it is possible to physically distinguish the start of a fall from a simple shock on the basis of the size of the scalar of the difference between acceleration vectors.

In yet another aspect, if a value of the evaluation function is represented by A, accelerations in the three axis directions at the steady time are represented by $(a_{x0}, a_{y0}, a_{z0})$ and accelerations at the fall determination time are represented by $(a_x, a_y, a_z)$, relations among the A, the $(a_{x0}, a_{y0}, a_{z0})$, and the $(a_x, a_y, a_z)$ are represented by $A=(a_x-a_{x0})^2+(a_y-a_{y0})^2+(a_z-a_{z0})^2$.

Thus, there is no longer the need to perform a root calculation involving a heavy calculation load. As a result, even if the calculation capability is low, a determination can be rapidly made.

In another aspect, if a value of the evaluation function is represented by A, accelerations in the three axis directions at the steady time are represented by $(a_{x0}, a_{y0}, a_{z0})$ and accelerations at the fall determination time are represented by $(a_x, a_y, a_z)$, relations among the A, the $(a_{x0}, a_{y0}, a_{z0})$, and the $(a_x, a_y, a_z)$ are represented by the following equation:

$$A=|a_x-a_{x0}|+|a_y-a_{y0}|+|a_z-a_{z0}|.$$

Thus, there is no longer the need to perform a root calculation or a square calculation involving a heavy calculation load. As a result, even if the calculation capability is low, a determination can be rapidly made.

According to another aspect, the steady time is before the time when a differential value of the absolute value of an acceleration detected by the acceleration detection means reaches a predetermined negative threshold, and the fall determination time is after the time when a differential value of the absolute value of an acceleration detected by the acceleration detection means falls below a predetermined threshold in a negative direction.

Thus, monitoring of a differential value of the absolute value of an acceleration at a steady time and at a fall determination time and monitoring of an acceleration by the fall start determination means can be sequentially performed in this time order. Therefore, there is no need to make determinations simultaneously on the basis of multiple thresholds. Also, there is no need to make determinations simultaneously on the basis of an acceleration and a differential value of the acceleration. In particular, the problems, such as one where when a determination is made using software, the calculation load put on the CPU is increased and the processing time is increased are resolved.

In another aspect, the steady time is before the time when the absolute value of a differential value of an acceleration detected by the acceleration detection means reaches a predetermined threshold, and the fall determination time is after the time when the absolute value of a differential value of an acceleration detected by the acceleration detection means exceeds a predetermined threshold.

Thus, monitoring of the absolute value of a differential value of an acceleration at a steady time and that at the time of a fall determination and monitoring of an acceleration by the fall start determination means may be sequentially performed in this time order. Therefore, there is no need to make determinations simultaneously on the basis of multiple thresholds. Also, there is no need to make determinations simultaneously on the basis of an acceleration and a differential value of the acceleration. In particular, the problems, such as one where when a determination is made using software, the calculation load put on the CPU is increased and the processing time is increased are resolved.

(In another aspect, a fall detection device can include fall-in-progress detection means that detects whether the fall detection device is placed in a fall-in-progress state. The fall-in-progress state is a state in which a low-gravity state continues for a predetermined time or more, the low-gravity state being a state in which the absolute value of the acceleration falls below a predetermined threshold within a predetermined time or falls within a predetermined range lower than a steady state after the fall start determination means considers that the fall detection device has been put into a fall start state.

In yet another aspect, a fall detection device can include fall-in-progress detection means that detects whether the fall detection device is placed in a fall-in-progress state. The fall-in-progress state is a state in which a low-gravity state continues for a predetermined time or more, the low-gravity state being a state in which a differential value of the absolute value of the acceleration exceeds a predetermined threshold within a predetermined time or falls within a predetermined range near 0 after the fall start determination means considers that the fall detection device has been put into a fall start state.

In another aspect, a fall detection device can include fall-in-progress detection means that detects whether the fall detection device is placed in a fall-in-progress state. The fall-in-progress state being a state in which a low-gravity state continues for a predetermined time or more, the low-gravity state being a state in which the absolute value of the differential value of the acceleration falls below a predetermined threshold within a predetermined time or falls within a predetermined range near 0 after the fall start determination means considers that the fall detection device has been put into a fall start state.

Thus, independently of a determination of the start of a fall made by the fall start determination means, the fall-in-progress state detection means can properly detect that the fall detection device has moved into a low-gravity state. This makes it possible to perform a proper process corresponding to a fall. Also, it is possible to perform processes corresponding to two stages of states with respect to a fall, that is, it is possible to determine the start of a fall using the fall start determination means and to detect a fall-in-progress state using the fall-in-progress state detection means.

In yet another embodiment, a magnetic disk drive can include the above-mentioned fall detection device, and further include a head that records data into a magnetic disk or reads data from the magnetic disk, and head evacuation means that evacuates the head to an evacuation area when the fall detection device detects the fall start state.

Thus, the magnetic disk drive can be protected. Also, a problem that the response speed of the magnetic disk drive in use is reduced can be resolved, since there is little erroneous detection.

In another embodiment, a magnetic disk drive can include the above-mentioned fall detection device, and further include a head that records data into a magnetic disk or reads data from the magnetic disk, and head evacuation means that evacuates the head to an evacuation area when the fall detection device detects the fall-in-progress state.

Thus, the magnetic disk drive can be protected. Also, a problem that the response speed of the magnetic disk drive in use is reduced can be resolved, since there is little erroneous detection.

In another aspect, a portable electronic apparatus includes the above-mentioned fall detection device and a device that is allowed to undergo a shock-proof process. The portable electronic device includes shock-proof process means that performs the shock-proof process on the device when the fall detection device detects the fall start state.

Thus, a process in preparation for a fall start state can be performed. As a result, the device that is allowed to undergo a shock-proof process can be effectively controlled so that the safety of the portable electronic apparatus can be enhanced.

In another aspect, a portable electronic apparatus includes the above-mentioned fall detection device and a device that is allowed to undergo a shock-proof process. The portable electronic device includes shock-proof process means that performs the shock-proof process on the device when the fall detection device detects the fall-in-progress state.

Thus, when a fall-in-progress state is detected, a process corresponding to the fall can be performed. As a result, the device that is allowed to undergo a shock-proof process can be effectively controlled so that the safety of the portable electronic apparatus can be enhanced.

Embodiments of a fall detection device consistent with the invention can allow for reducing processing load when making a determination using software, can reliably determine the start of a fall, can make a fall prediction as necessary, and can be configured with a magnetic disk drive and a portable electronic apparatus.

DETAILED DESCRIPTION

Figure 1:
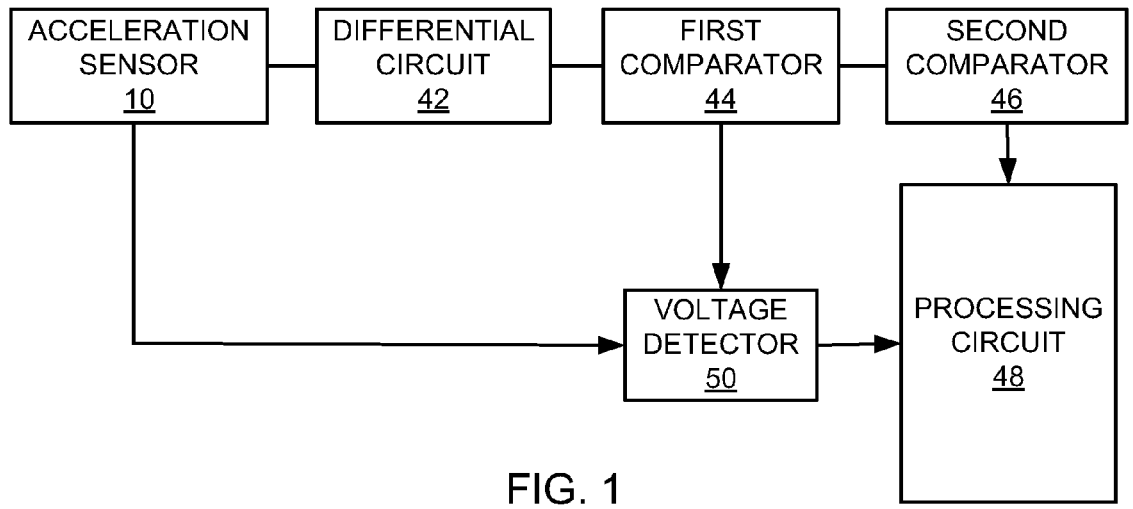
FIG. 1 is a block diagram showing a configuration of a conventional fall detection device.
Figure 2:
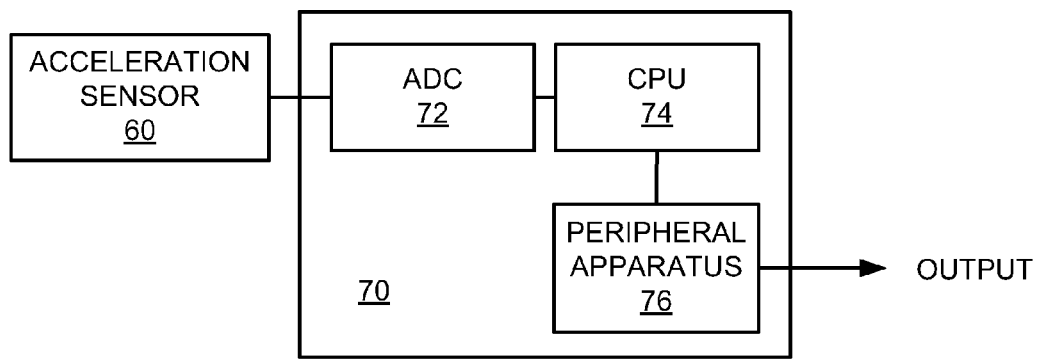
FIG. 2 is block diagram showing a configuration of a fall detection device according to an exemplary embodiment.

FIG. 2 is block diagram showing a configuration of a fall detection device 100 according to an exemplary embodiment. The fall detection device 100 includes an acceleration sensor 60 that detects an acceleration and outputs an analog voltage signal corresponding to the acceleration, an A/D converter 72 that converts a voltage outputted from the acceleration sensor 60 into digital data, a peripheral device 76 such as a ROM/RAM or an external interface, and a CPU 74 that detects whether a fall has occurred, on the basis of data outputted from the A/D converter 72 and outputs the detection result to the outside (host apparatus). The A/D converter 72, peripheral device 76, and CPU 74 are included in a single-chip microcomputer 70.

Even if it is undetermined in which direction a fall is directed, accelerations in three-dimensional directions are detected to detect the fall, and the fall is detected on the basis of these accelerations. In this case, specifically, the acceleration sensor 60 in FIG. 2 includes three acceleration sensors that detect an acceleration in an X-axis direction, an acceleration in a Y-axis direction, and an acceleration in a Z-axis direction, respectively. These axis directions are orthogonal to one another. The A/D converter 72 converts voltages outputted from the acceleration sensors into pieces of digital data. For example, if the accelerations in the axis directions are represented by ax, ay, and az, respectively, in a case where the absolute value of an acceleration is obtained, the CPU 74 obtains the absolute value |a| of an acceleration a serving as a vector by performing an operation $|a|=\sqrt{(ax^2+ay^2+az^2)}$.

As the acceleration sensors, acceleration sensors of various types such as piezoelectric-type, piezoelectric resistance-type, and capacity-type can be used.

Figure 3:
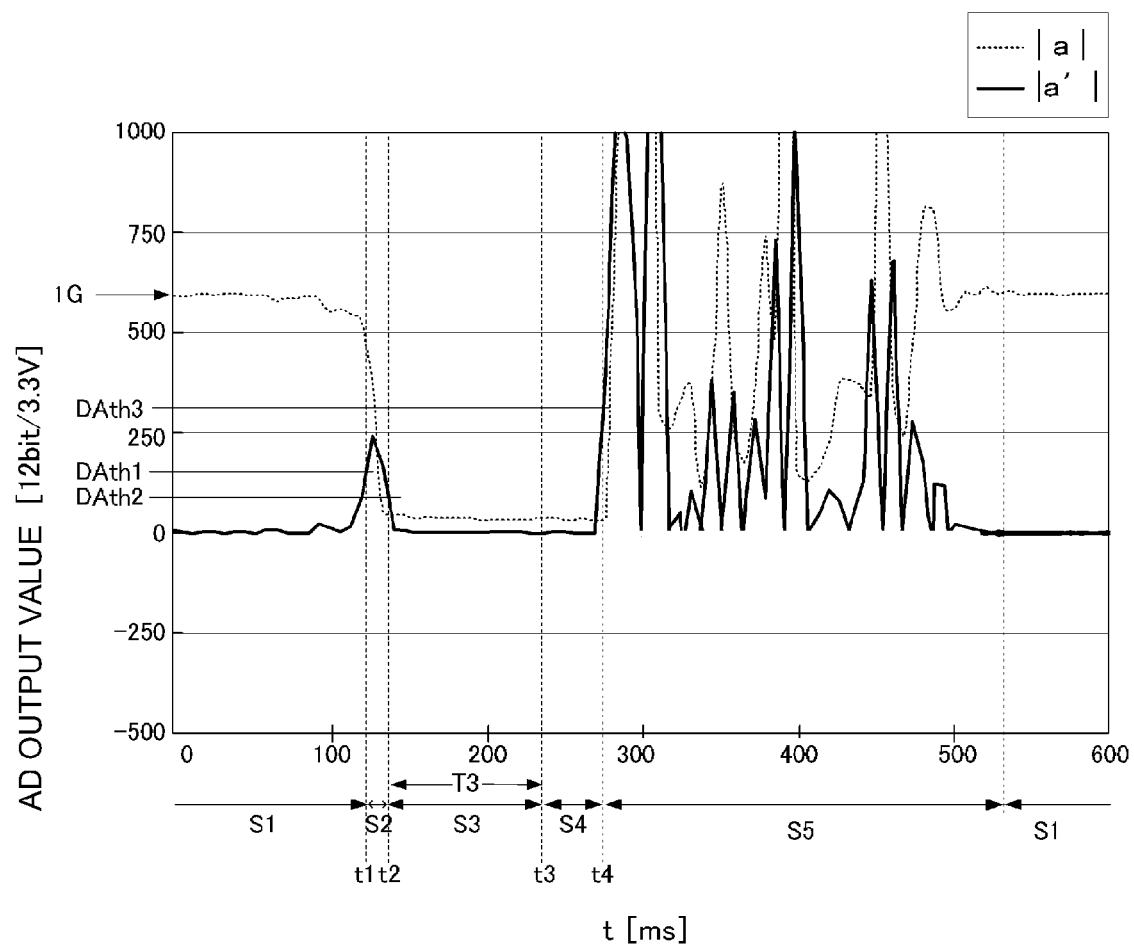
FIG. 3 is a drawing showing an example of variations in the absolute value of an acceleration detected by an acceleration sensor of the fall detection device shown in FIG. 2 and variations in the absolute value of the differential value of the acceleration and showing transition states from a first stage S1 to a fifth stage S5.

FIG. 3 shows an example of time lapses of the absolute value of an acceleration and the absolute value of the differential value of the acceleration received by the fall detection device 100 before and after a fall. The lateral axis is an elapsed time t [ms]. The longitudinal axis is the absolute value |a| of an acceleration and the absolute value |a'| of the differential value of the acceleration. The absolute value |a| of the acceleration is the square root of the sum of the squares of the accelerations (the values of outputs produced by the A/D converter 72) in the three axis directions. The absolute value |a'| of the differential value of the acceleration is the absolute value (square root of the sum of the squares) of the value of the difference among the accelerations in the three axis directions per unit time.

In FIG. 3, the device is placed in a first stage S1 "steady state" before the absolute value |a'| of the differential value of the acceleration reaches a threshold DAth1. Therefore, the acceleration is the acceleration of gravity (=1 G) and the value of an output produced by the A/D converter at this time is about 600. Since the absolute value |a| of the acceleration is approximately constant, the absolute value |a'| of the differential value of the acceleration is approximately 0. Subsequently, when a fall starts at a time, the |a| of the acceleration decreases abruptly and the absolute value |a'| of the differential value of the acceleration increases.

After the absolute value |a'| of the differential value of the acceleration exceeds the threshold DAth1, it is considered that the device may have been put into a second stage S2 "fall start state". Since the absolute value |a'| of the differential value of the acceleration also varies in the shape of a mountain due to a simple shock as described later, whether the device has actually been put into the second stage S2 "fall start state" is determined on the basis of the result of performance of another determination to be described later.

Subsequently, the fall detection device is put into a low-gravity state (gravity-free state) due to a free movement and thus the absolute value |a| of the acceleration and the absolute value |a'| of the differential value of the acceleration both become 0. However, if an offset exists in the output produced by the acceleration sensor 60, the absolute value |a| of the acceleration does not completely become 0 unlike in FIG. 3.

If the absolute value |a'| of the differential value of the acceleration falls below a threshold DAth2 or falls within a predetermined range near 0, it is considered that the device may have been put into a third stage S3 "low-gravity state." As described later, the absolute value |a'| of the differential value of the acceleration also varies in the shape of a mountain due to a simple shock; therefore, another determination to be described later is made to consider that the device has been put into the third stage S3 "low-gravity state". Note that by determining whether the absolute value |a| of the acceleration has fallen below a predetermined threshold or has fallen within a predetermined range lower than a steady state, it may be considered that the device may have been put into the third stage S3 "low-gravity state".

When a given time T3 elapses, it is considered that the device has been put out of this low-gravity state into a "fall-in-progress state". A fourth stage S4 is the "fall-in-progress state."

Subsequently, the fall detection device (an electronic apparatus including the fall detection device) collides with the floor or the like and thus the absolute value |a| of the acceleration of the fall detection device abruptly increases. For example, the fall detection device repeatedly bounds and thus the absolute value |a| of the acceleration significantly varies. A fifth stage S5 in the graph shows this "fall shock state."

Subsequently, when the fall detection device ceases to bound or a human lifts up the electronic apparatus and thus the acceleration is stabilized, the fall detection device returns to the first stage S1 "steady state."

Note that the fifth stage S5 appears for a relatively long time since the fall detection device falls onto a cushion material in an example shown in FIG. 3.

Figure 4A:
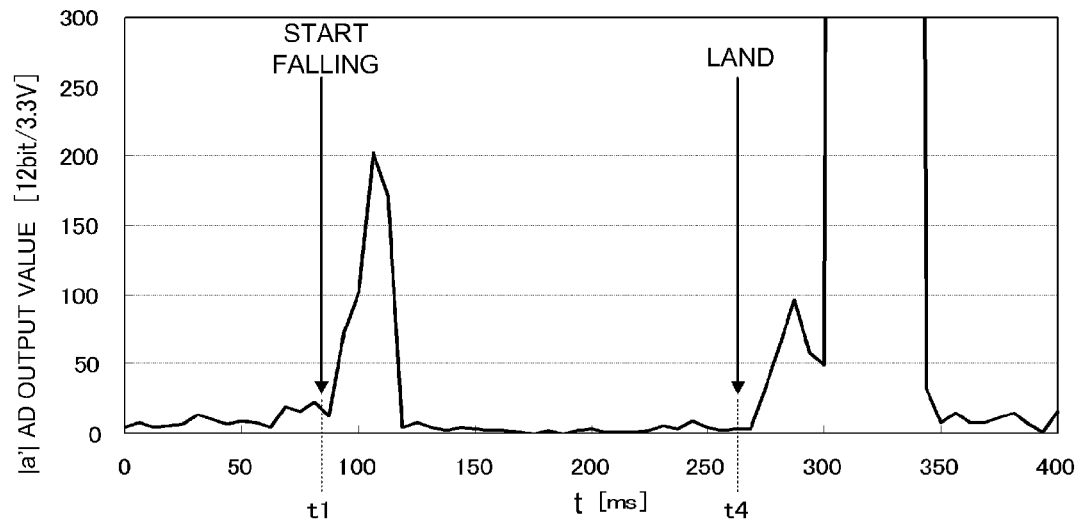
FIG. 4 includes graphs showing variations in the absolute value of a differential value of an acceleration due to a fall and those due to a simple shock.
Figure 4B:
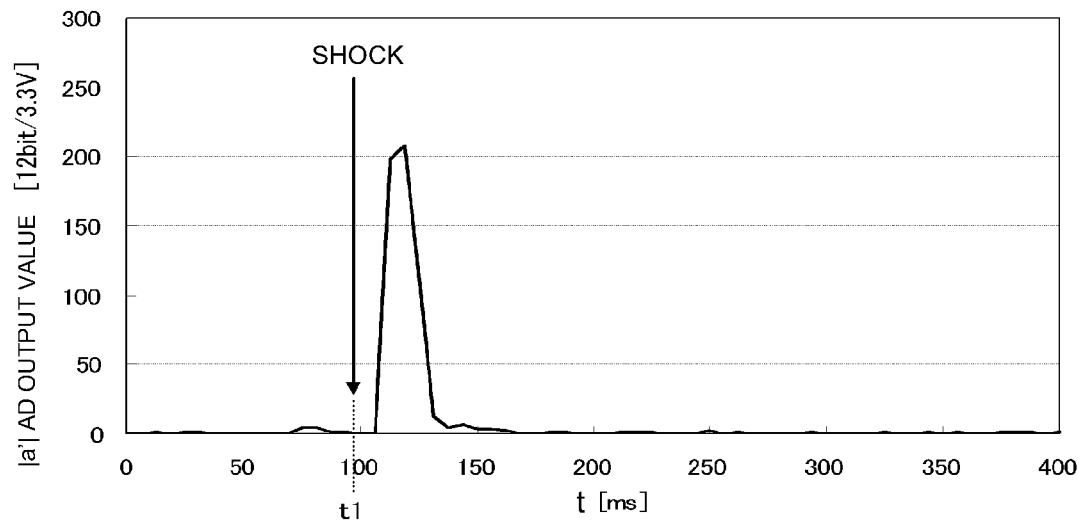

FIGS. 4A and 4B show examples of a time lapse of the absolute value |a'| of the differential value of the acceleration in a case where a simple shock is given to the fall detection device, as described above.

FIG. 4A is a case of a fall and FIG. 4B is a case of a simple shock. In the case of a fall, as shown in FIG. 4A, immediately after a fall start time t1, the absolute value |a'| of a differential value of an acceleration appears in the shape of a mountain. Subsequently, when the fall detection device lands at a time t4, the absolute value |a'| of the differential value of the acceleration significantly varies.

On the other hand, in the case of a simple shock, as shown in FIG. 4B, immediately after a shock occurs (for example, when a finger is slightly tapped on the sensor) at the time t1, the absolute value |a'| of a differential value of an acceleration appears in the shape of a mountain. The shape of this mountain may extremely resemble a mountain shape that appears when a fall occurs. Of course, the simple shock involves no landing, so variations as shown at a time t4 and later in FIG. 4A do not appear. From the fact that there have been no variations due to a landing, it is consequently understood that a simple shock has occurred. However, if the fall detection device waits for such a long time to elapse and then makes a determination, it would be too late if a fall has actually occurred. Hence, whether the mountain shaped absolute value |a'| of the differential value of the acceleration is due to a fall or due to a simple shock must be determined immediately after the absolute value |a'| has appeared in the shape of a mountain.

Figure 5A:
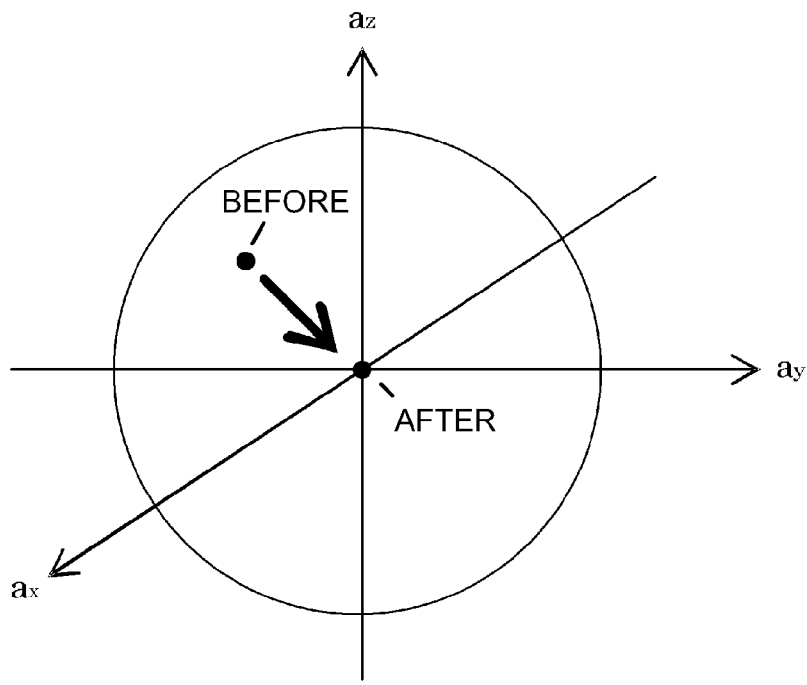
FIG. 5 includes graphs showing variations in the acceleration vector due to a fall and those due to a simple shock.
Figure 5B:
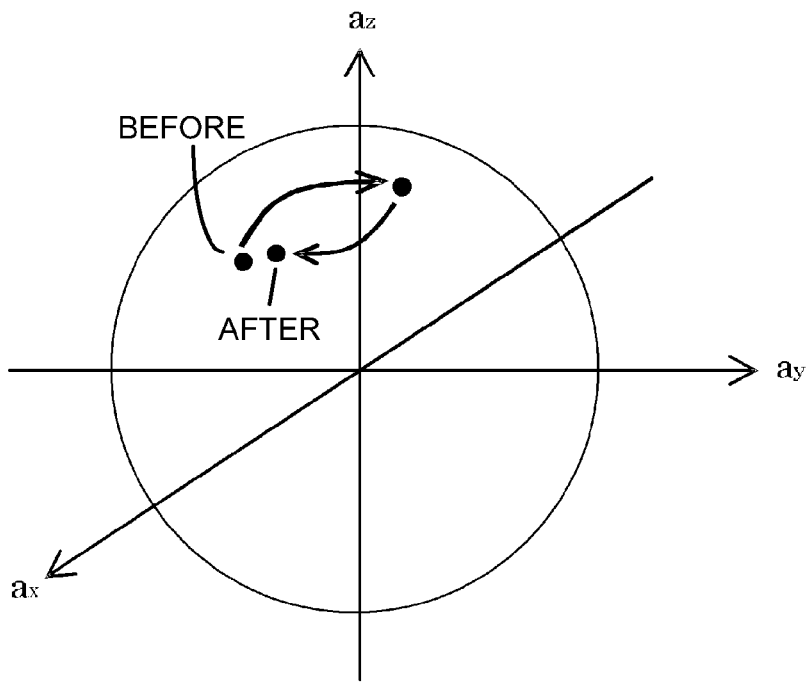

For this reason, a determination whether the mountain is due to a fall or due to shock is made on the basis of variations in the acceleration. FIGS. 5A and 5B include graphs showing a method for making the determination.

The accelerations in the three orthogonal axis directions are represented by ($a_x$, $a_y$, $a_z$). FIG. 5A shows variations in the acceleration vector before a fall starts and those after the fall starts. FIG. 5B shows variations in the acceleration vector before a shock starts and those after the shock starts. As shown in FIG. 5A, the acceleration sensor is receiving a gravity acceleration (1 G) before the fall starts. Therefore, if the acceleration vector is shown in space of acceleration, it exists at a point on a sphere of 1 G. When the fall starts, the acceleration sensor is put into a low-gravity state (0 G). Therefore, the acceleration vector moves to the origin point on the acceleration space.

On the other hand, when a simple shock occurs, the acceleration sensor departs from a 1 G sphere due to the shock only for a moment as shown in FIG. 5B and immediately returns onto the sphere.

For this reason, the acceleration vector immediately before the fall and the acceleration vector at the fall determination time are compared, and if the distance (the scalar of the difference between the acceleration vectors) over which the acceleration vector has moved on the acceleration space is equal to or larger than a threshold (e.g., 0.5 G), the mountain can be considered a fall. If the distance is less than the threshold, it is determined that the mountain is not due to a fall, considering that the mountain is due to a simple shock.

The CPU 74 shown in FIG. 2 detects a fall on the basis of the value of an output produced by the A/D converter 72 shown in the drawing. FIGS. 6 to 9 are flowcharts showing processes for that purpose.

Figure 6:
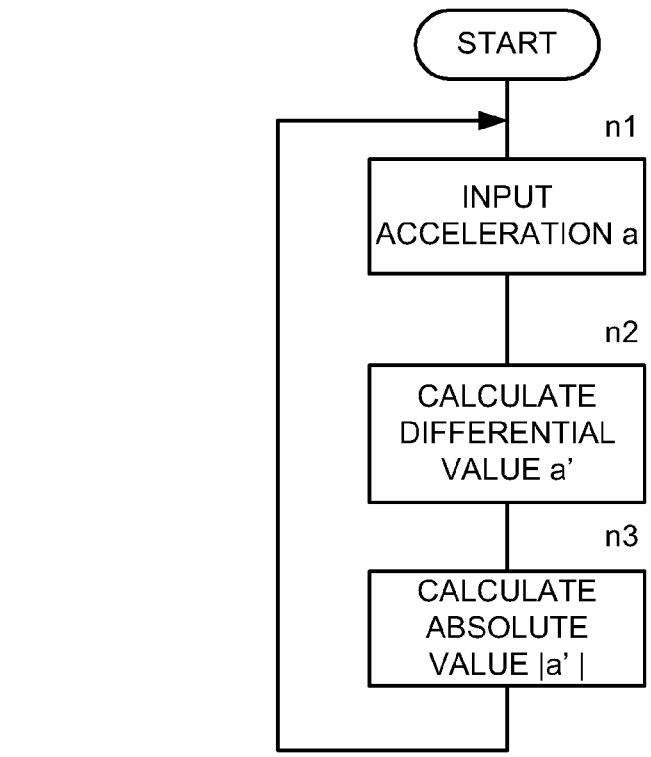
FIG. 6 is a flowchart showing a part of the contents of a process performed by a control section.

FIG. 6 shows processes for generating data to serve as the base for detecting a fall on the basis of an output produced by the acceleration sensor. First, the value (the value of the acceleration a) of an output produced by the A/D converter 72 is inputted (n1). Subsequently, the differential value a' of the acceleration is calculated (n2). Specifically, the difference between the last acceleration and the current acceleration is obtained as the differential value a' of the acceleration. Subsequently, the absolute value |a'| of the obtained differential value is calculated (n3), that is, the scalar of a' is obtained. The process shown in FIG. 6 is repeatedly performed at every sampling cycle.

Figure 7:
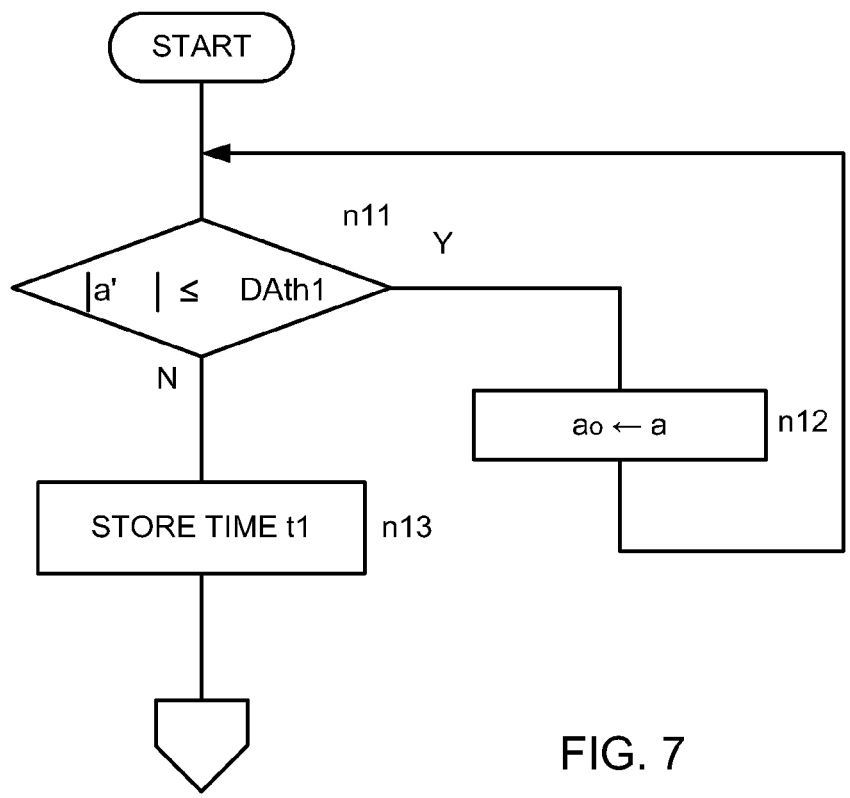
FIG. 7 is a flowchart showing an exemplary process in the first stage.

FIG. 7 is a flowchart showing processes in the first stage. First, whether the absolute value |a'| of the differential value of the acceleration falls below the threshold DAth1 is determined. If the absolute value |a'| falls below the threshold DAth1, then acceleration a is stored as an acceleration ao at a steady time (n11→n12).

If the absolute value |a'| of the differential value of the acceleration exceeds the threshold DAth1, then time t1 is stored (n13), and the process moves to the second stage.

Figure 8:
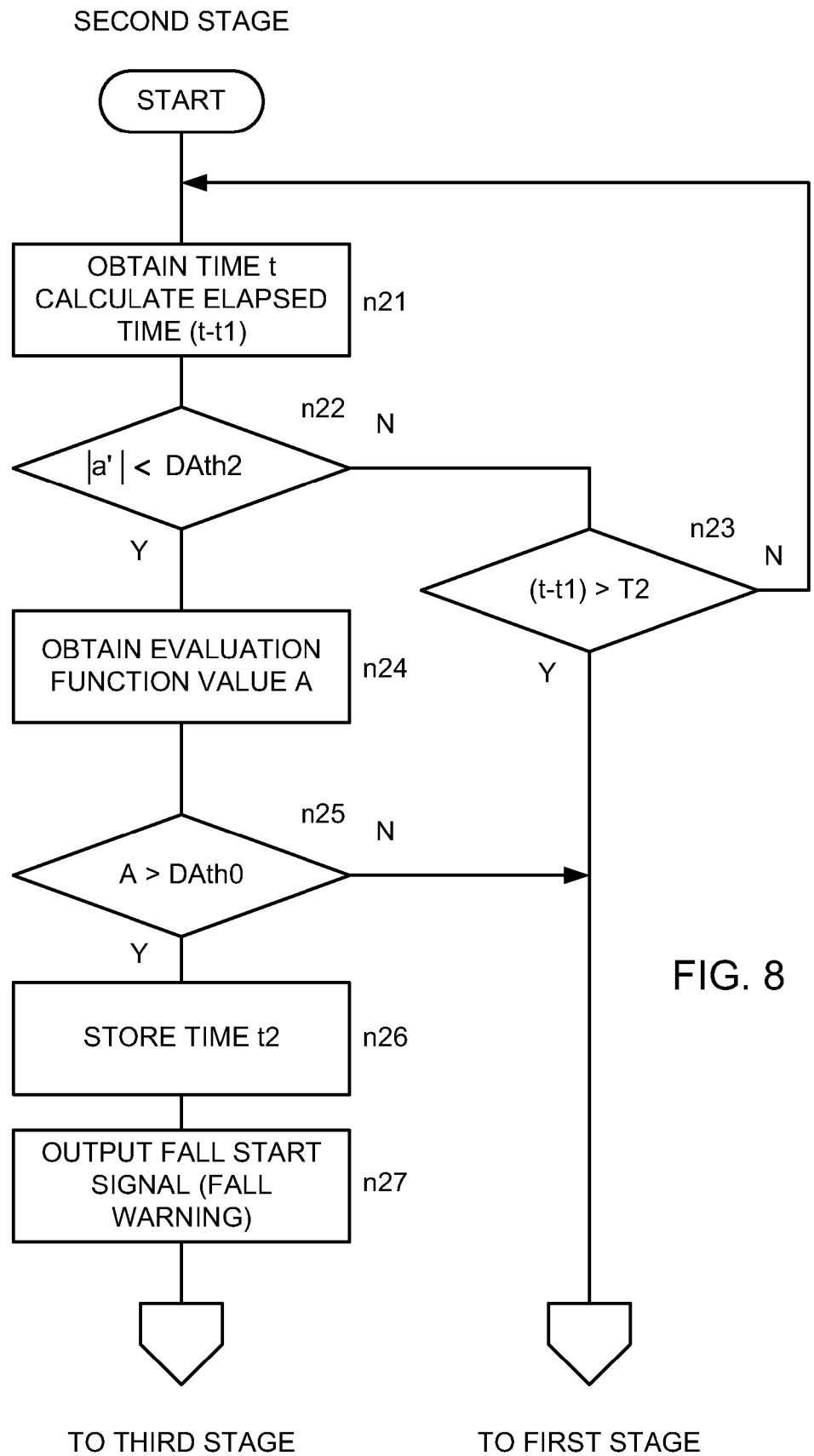
FIG. 8 is a flowchart showing an exemplary process in the second stage.

FIG. 8 is a flowchart showing processes in the second stage.

First, the current time t is obtained, and a time (t−t1) that has elapsed since the movement to the second stage is calculated (n21).

Whether the absolute value |a'| of the differential value of the acceleration falls below the threshold DAth2 is determined. If the absolute value |a'| falls below the threshold, an evaluation value A is obtained on the basis of a predetermined evaluation function by which the evaluation value A is increased as the difference increases between the acceleration ao ($a_{x0}$, $a_{y0}$, $a_{z0}$) at a steady time and the acceleration a ($a_x$, $a_y$, $a_z$) at the time when a fall determination (n22→n24). For example, the absolute value |a'| of the difference between the acceleration ao at a steady time and the acceleration a at the time when a fall is determined can be defined as an evaluation value A. If the evaluation value A exceeds a threshold DAth0, the then time t2 is stored and a fall start signal (fall warning) is outputted (n25→n26→n27). Subsequently, the process moves to the third stage. As for the determination in the process n22, whether the absolute value |a'| of the differential value of the acceleration falls within a predetermined range near 0 may be determined. Also, whether the absolute value |a| of the acceleration falls below a predetermined threshold or falls within a predetermined range lower than a steady state may be determined.

If the evaluation value A does not exceed the threshold DAth0, it is considered that mountain-shaped variations in the absolute value |a'| of the differential value of the current acceleration a are due to a simple shock, and the process returns to the first stage (n25→first stage).

If the absolute value |a'| of the differential value of the acceleration does not fall below the threshold DAth2 within a prescribed time T2, it is considered that light shocks have been simply given to the fall detection device (that is, it is considered that the variations are not due to the start of a fall) and the process returns to the first stage (n23→first stage).

Figure 9:
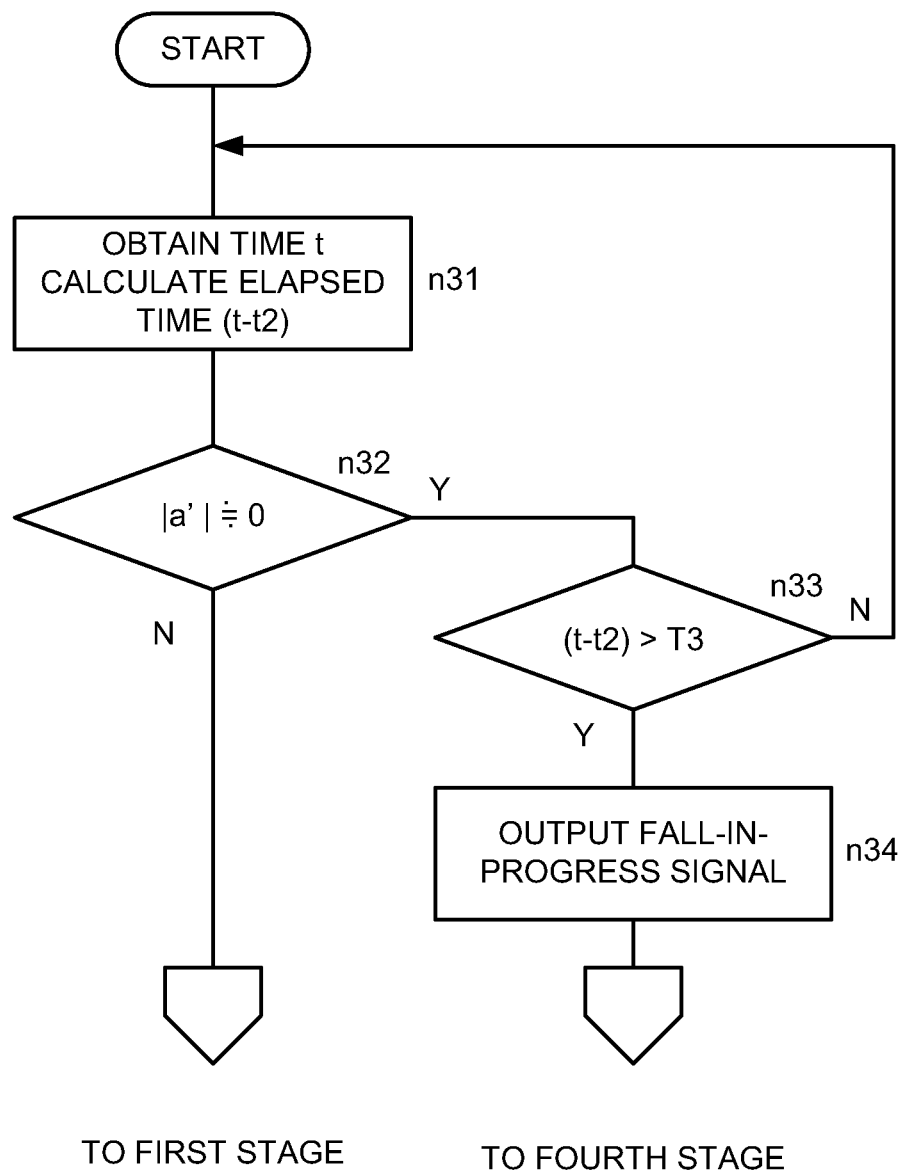
FIG. 9 is a flowchart showing an exemplary process in the third stage.

FIG. 9 is a flowchart showing processes in the third stage. First, the current time t is obtained, and a time (t−t2) that has elapsed since the movement to the third stage is calculated (n31). Then, whether the absolute value |a'| of the differential value of the acceleration has become approximately 0 is determined. If the time when the absolute value has become approximately 0 exceeds a prescribed value T3, a fall-in-progress signal indicating that a fall has started and is in progress is outputted (n32→n33→n34). Then, the process moves to the fourth stage.

If the absolute value |a'| of the differential value of the acceleration does not become approximately 0 within the prescribed value T3, it is considered that this phenomenon that has caused the movement of the third stage is not due to a fall, and the process returns to the first stage (n32→first stage).

Figure 10:
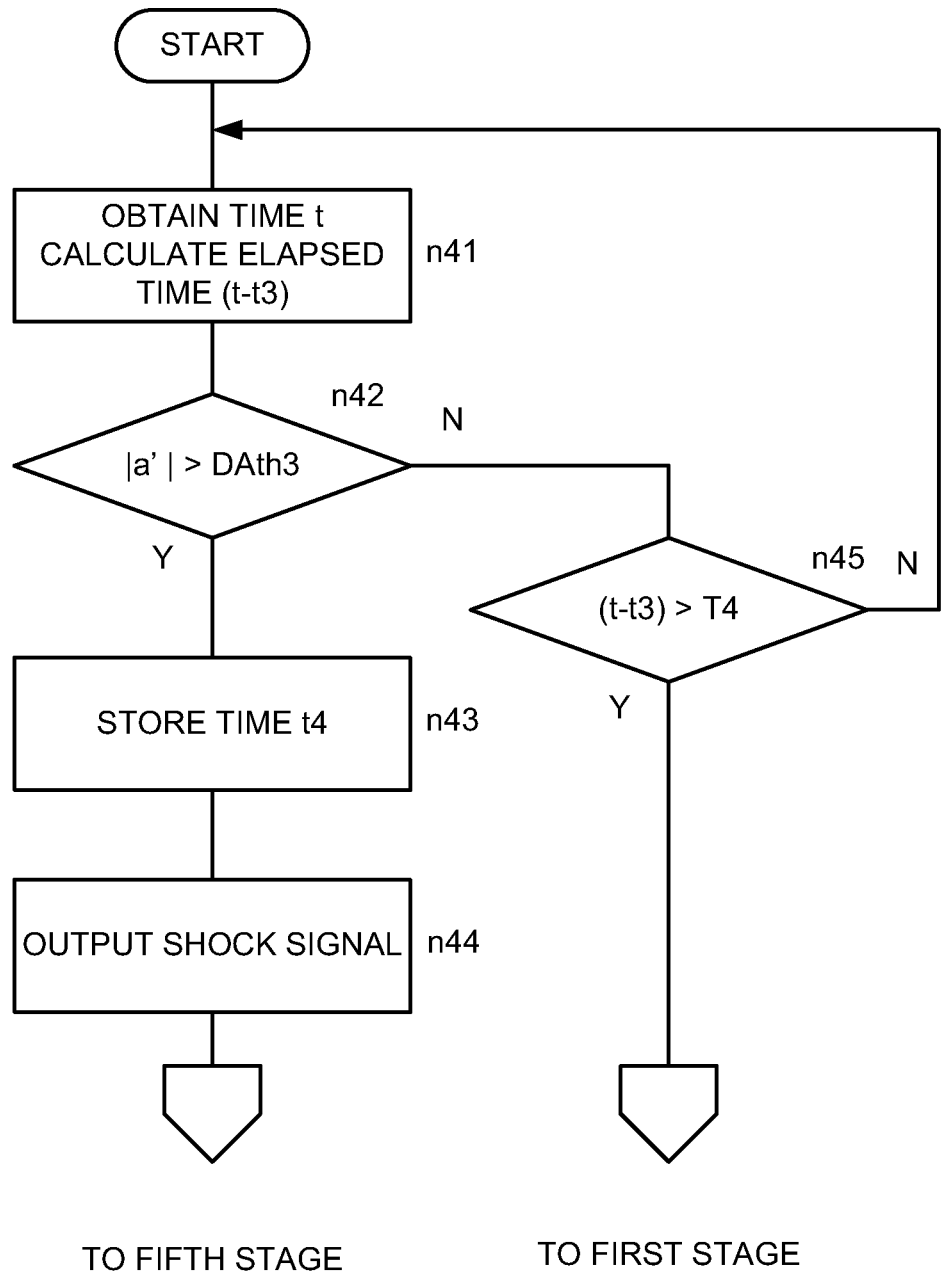
FIG. 10 is a flowchart showing an exemplary process in the fourth stage.

FIG. 10 is a flowchart showing processes in the fourth stage. First, the current time t is obtained, and a time (t−t3) that has elapsed since the movement to the third stage is calculated (n41). Then, whether the absolute value |a'| of the differential value of the acceleration exceeds a threshold DAth3 is determined. If the absolute value |a'| exceeds the threshold, it is considered that a large shock has occurred due to a landing, and the then time t4 is stored and a shock signal is outputted. The process returns to the first stage (n42→n43→n44).

Even if the absolute value |a'| of the differential value of the acceleration does not exceed the threshold DAth3, it is considered that a shock has been avoided, provided that the elapsed time (t−t3) exceeds a prescribed time T4. The process returns to the first stage (n45→first stage).

Figure 11:
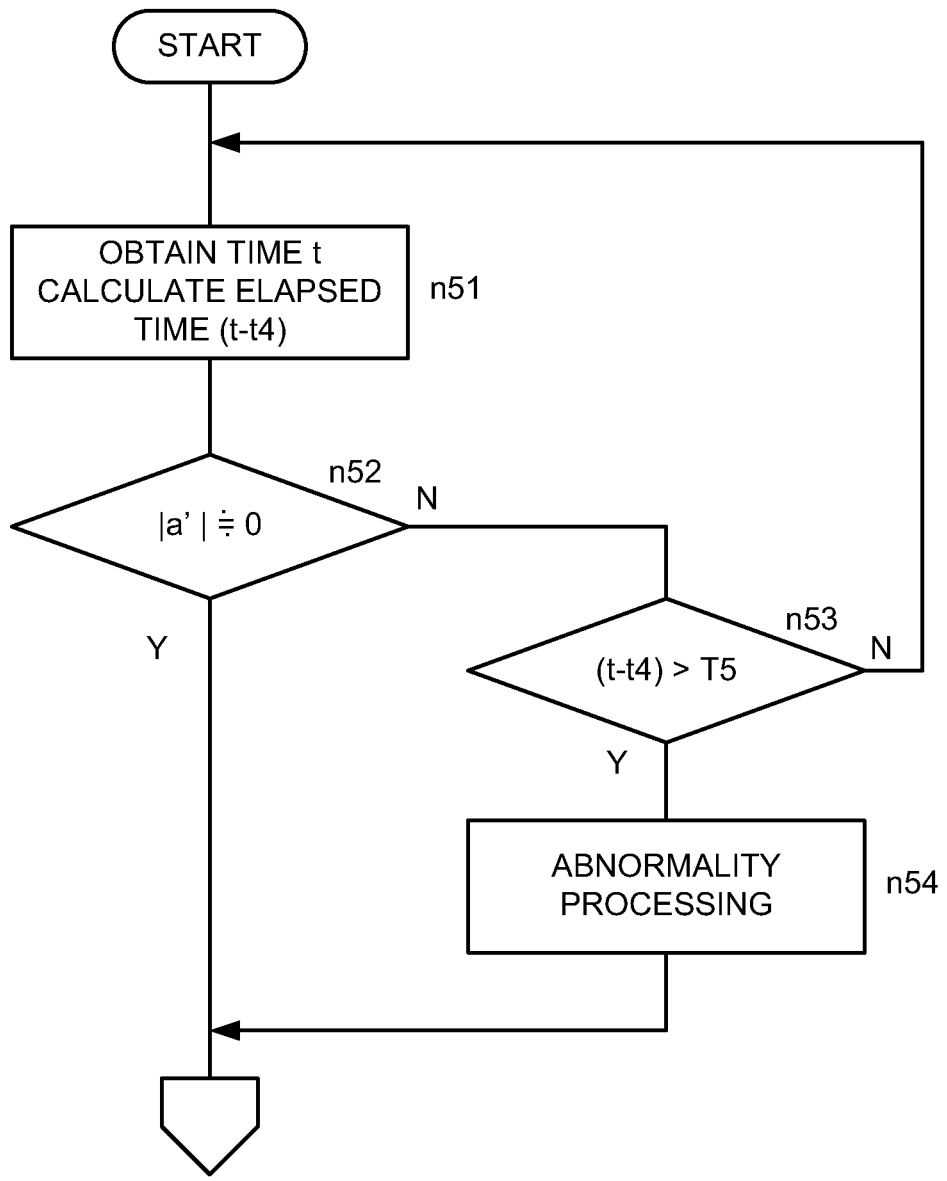
FIG. 11 is a flowchart showing processes in the fifth stage.

FIG. 11 is a flowchart showing processes in the fifth stage. First, the current time t is obtained, and a time (t−t4) that has elapsed since the movement to the fifth stage is calculated (n51). Then, if the absolute value |a'| of the differential value of the acceleration has become approximately 0, the process returns to the first stage, which a steady state (n51→n52→first stage). If the absolute value |a'| of the differential value |a'| of the acceleration does not become approximately 0 even after the elapsed time (t−t4) has elapsed for a predetermined time T5, for example, an abnormality process considering that the fall detection device has been put into an abnormal state due to a shock is performed (n53→n54).

While a determination is made with respect to each state on the basis of the absolute value of a differential value |a'| of an acceleration in the first exemplary embodiment, the same determination can be made on the basis of a differential value |a|' of the absolute value of an acceleration in a second exemplary embodiment. The overall configuration of a fall detection device is the same as that according to the first exemplary embodiment shown in FIG. 2. Also, the contents of the basic process to be performed by the CPU 74 in the second exemplary embodiment are the same as those in that embodiment.

Figure 12:
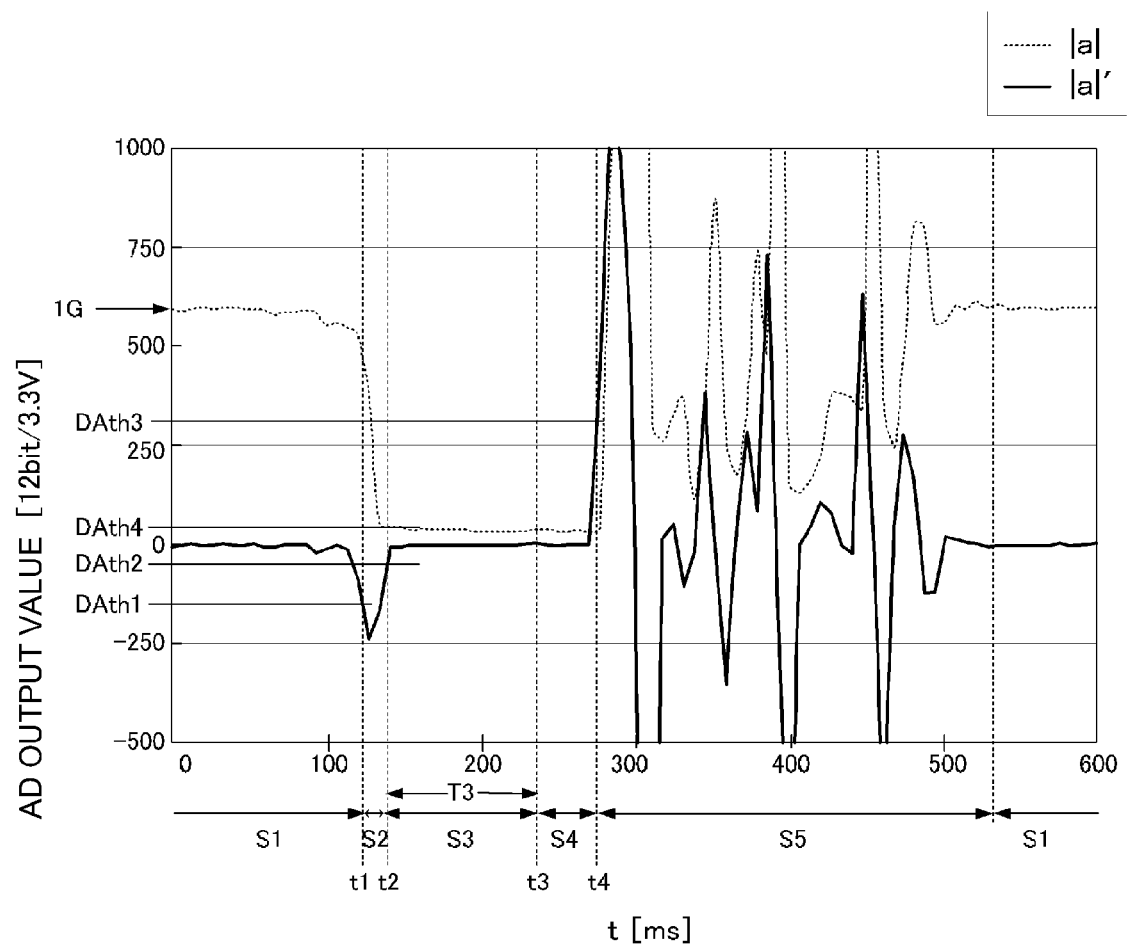
FIG. 12 is a drawing showing an example of variations in the absolute value of an acceleration detected by an acceleration sensor of a fall detection device according to a second embodiment and variations in differential value of the absolute value and showing transition states from a first stage S1 to a fifth stage S5.

FIG. 12 shows an example of time lapses of an acceleration and a differential value of the acceleration received by a fall detection device according to the second embodiment before and after a fall. The lateral axis is an elapsed time t [ms]. The longitudinal axis is the absolute value |a| of an acceleration and the absolute value |a|' of the differential value of the acceleration. The differential value |a|' of the absolute value of the acceleration is the value of the difference between the square roots of the sum of the squares of the accelerations (i.e., the values of outputs of the A/D converter 72) in the three axis directions per unit time.

In FIG. 12, it is considered that the fall detection device is placed in the first stage S1 "steady state" before the differential value |a|' of the absolute value of the acceleration reaches the threshold DAth1. Also, it is considered that the fall detection device is placed in the second stage S2 "fall start state" after the differential value |a|' of the absolute value of the acceleration falls below the threshold DAth1.

Subsequently, when |a|' falls within the range from the threshold DAth2 to a threshold DAth4, it is considered that the fall detection device has been put into the third stage S3 "low-gravity state." As described above, by determining whether |a|' has fallen within the predetermined range rather than simply determining whether |a|' has exceeded the threshold DAth2, an erroneous determination that vibration of the device is due to a fall is prevented.

When this low-gravity state has elapsed for the given time T3, it is considered that the fall detection device has been put into a "fall-in-progress state." The fourth stage S4 represents the "fall-in-progress state."

Subsequently, when the differential value |a|' of the absolute value of the acceleration exceeds the threshold DAth3, it is considered that the fall detection device has been put into the fifth stage S5 "fall shock state."

Subsequently, when |a|' has become approximately 0, it is considered that the fall detection device has been put into the first stage S1 "steady state."

Figure 13:
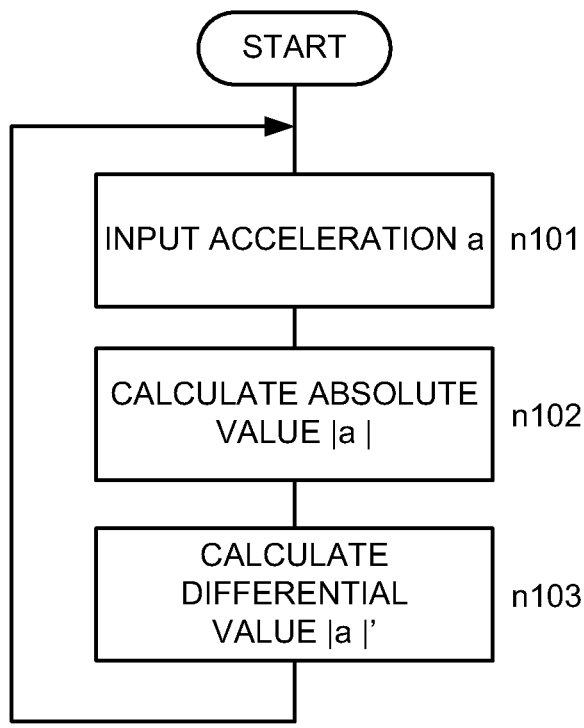
FIG. 13 is a flowchart showing a part of the contents of a process performed by a control section.

FIG. 13 shows processes for generating data to serve as the base for detecting a fall on the basis of an output produced by the acceleration sensor. First, the value (value of the acceleration a) of an output produced by the A/D converter 72 is inputted (n101). Subsequently, the absolute value |a| of the output value is calculated (n102), that is, the scalar of a is obtained. Subsequently, the difference between the absolute value of the last acceleration and the absolute value of the current acceleration is obtained as the differential value |a|' of the absolute value of the acceleration. The process shown in FIG. 13 is repeatedly performed at every sampling cycle.

Figure 14:
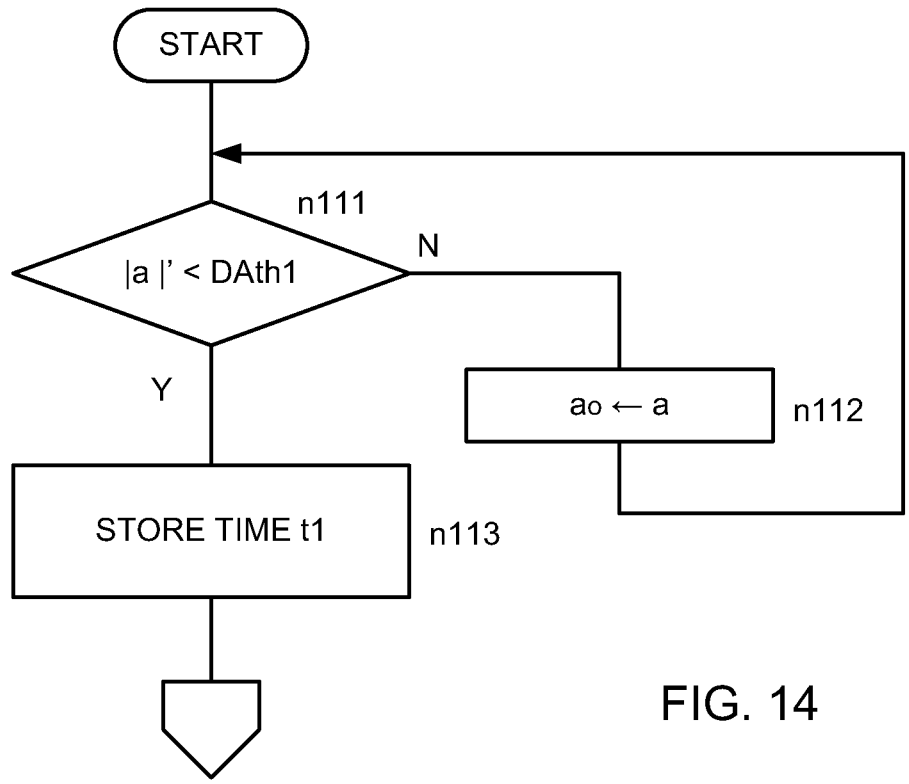
FIG. 14 is a flowchart showing an exemplary process the first stage.

FIG. 14 is a flowchart showing processes in the first stage.

First, whether the differential value |a|' of the absolute value of the acceleration falls below the threshold DAth1 is determined. If the differential value does not fall below the threshold, the then acceleration a is stored as the acceleration ao at a steady time (n111→n112).

If the differential value |a|' of the absolute value of the acceleration falls below the threshold DAth1, the then time t1 is stored and the process moves to the second stage (n113→second stage).

Figure 15:
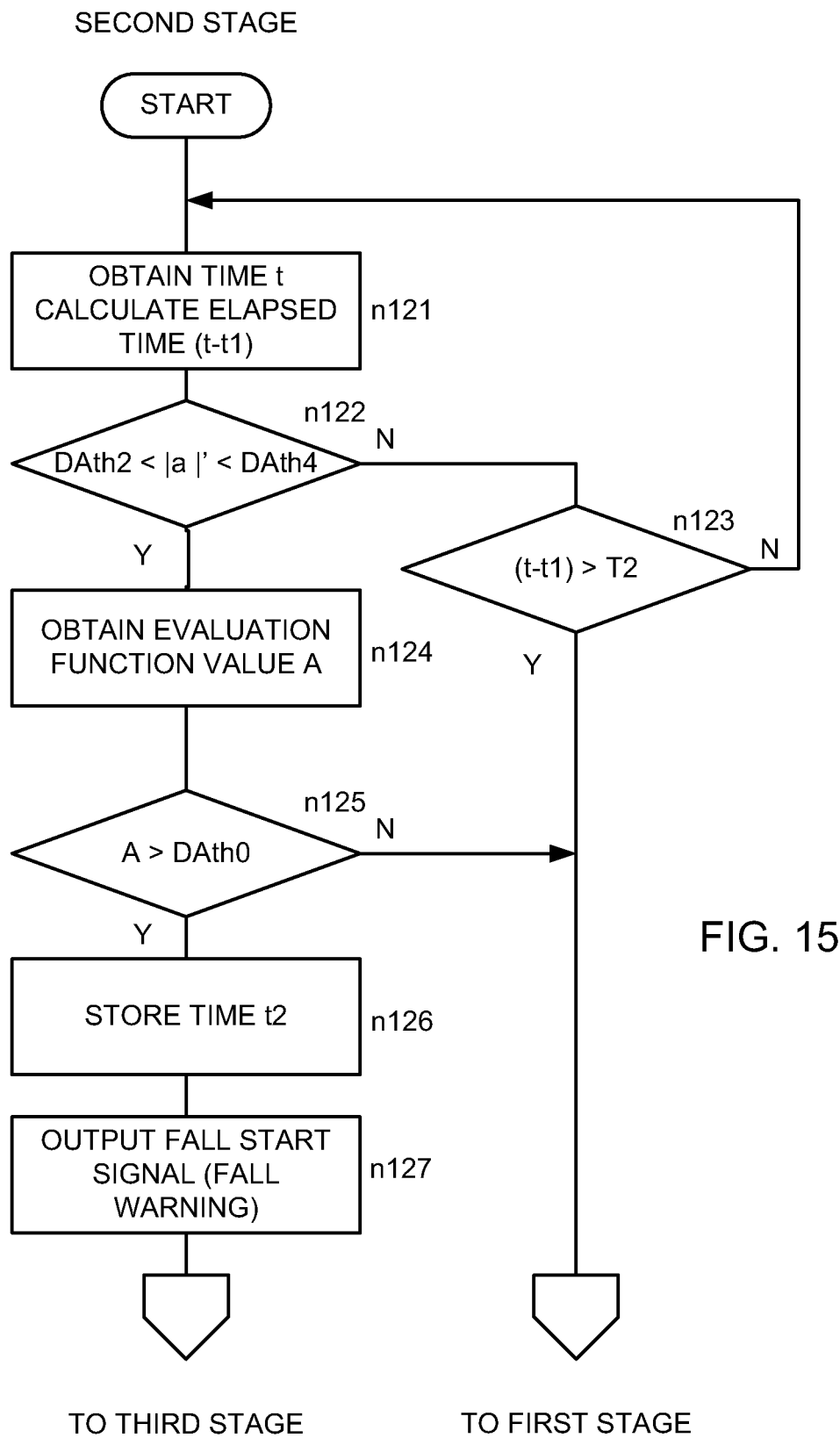
FIG. 15 is a flowchart showing an exemplary process in the second stage.

FIG. 15 is a flowchart showing processes in the second stage.

First, the current time t is obtained, and the time (t−t1) that has elapsed since the movement to the second stage is calculated (n121).

Next, a decision (n122) determines whether the differential value |a|' of the absolute value of the acceleration exceeds the threshold DAth2 and falls below DAth4. If the differential value falls within this range, the evaluation value A is obtained on the basis of a predetermined evaluation function by which the evaluation value is increased as the difference increases between the acceleration ao ($a_{x0}$, $a_{y0}$, $a_{z0}$) at a steady time and the acceleration a ($a_x$, $a_y$, $a_z$) at the fall determination time (n124). For example, the absolute value of the difference between the acceleration ao at a steady time and the acceleration a at the fall determination time is defined as the evaluation value A. If the evaluation value A exceeds the threshold DAth0, the then time t2 is stored and a fall start signal (fall warning) is outputted (n125→n126→n127). Subsequently, the process moves to the third stage.

Note that whether the differential value of the absolute value of the acceleration exceeds the predetermined threshold DAth2 may be determined in the process n122.

If the evaluation value A does not exceed the threshold DAth0, it is considered that mountain-shaped variations in the differential value |a|' of the absolute value of the current acceleration a are due to a simple shock as shown in FIG. 4B, and the process returns to the first stage (n125→first stage).

If the differential value |a|' of the absolute value of the acceleration does not fall within the above-mentioned range, whether the elapsed time (t−t1) exceeds the prescribed time T2 is determined (n122→n123). If the differential value |a|' of the absolute value of the acceleration does not fall within the above-mentioned range within the prescribed time T2, it is considered that light shocks have been simply continuously given (that is, it is considered that the variations are not due to the start of a fall) and the process returns to the first stage (n123→first stage).

Figure 16:
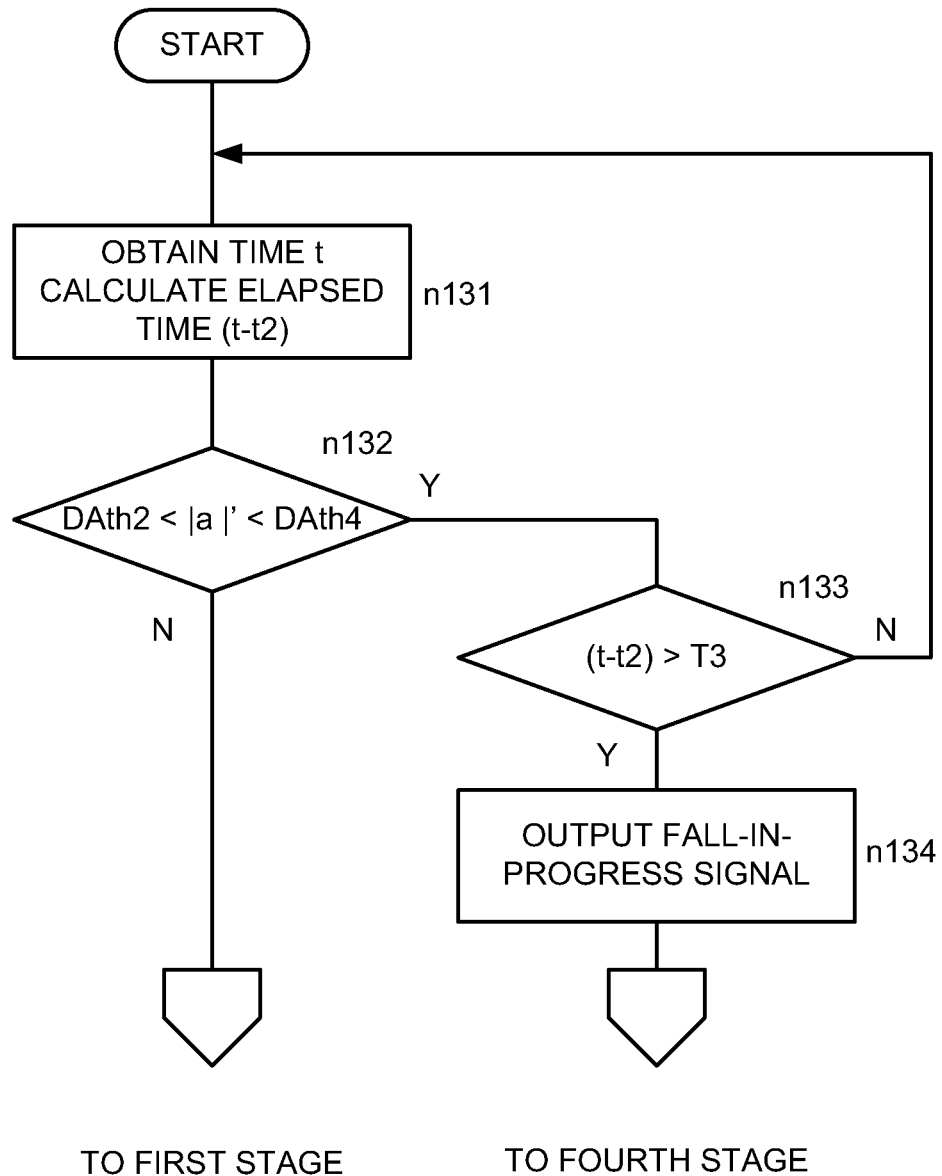
FIG. 16 is a flowchart showing an exemplary process in the third stage.

FIG. 16 is a flowchart showing processes in the third stage. First, the current time t is obtained, and the time (t−t3) that has elapsed since the movement to the third stage is calculated (n131). Then, whether the differential value |a|' of the absolute value of the acceleration exceeds the threshold DAth2 and falls below the DAth4 is determined. If a time that falls within this range continues for T3, a fall-in-progress signal indicating that a fall has started and is in progress is outputted (n132→n133→n134). Then, the process moves to the fourth stage.

If the differential value |a|' of the absolute value of the acceleration exceeds the above-mentioned range before reaching the prescribed value T3, it is considered that this phenomenon that has caused the movement of the third stage is not due to a fall and the process returns to the first stage (n132→first stage).

Figure 17:
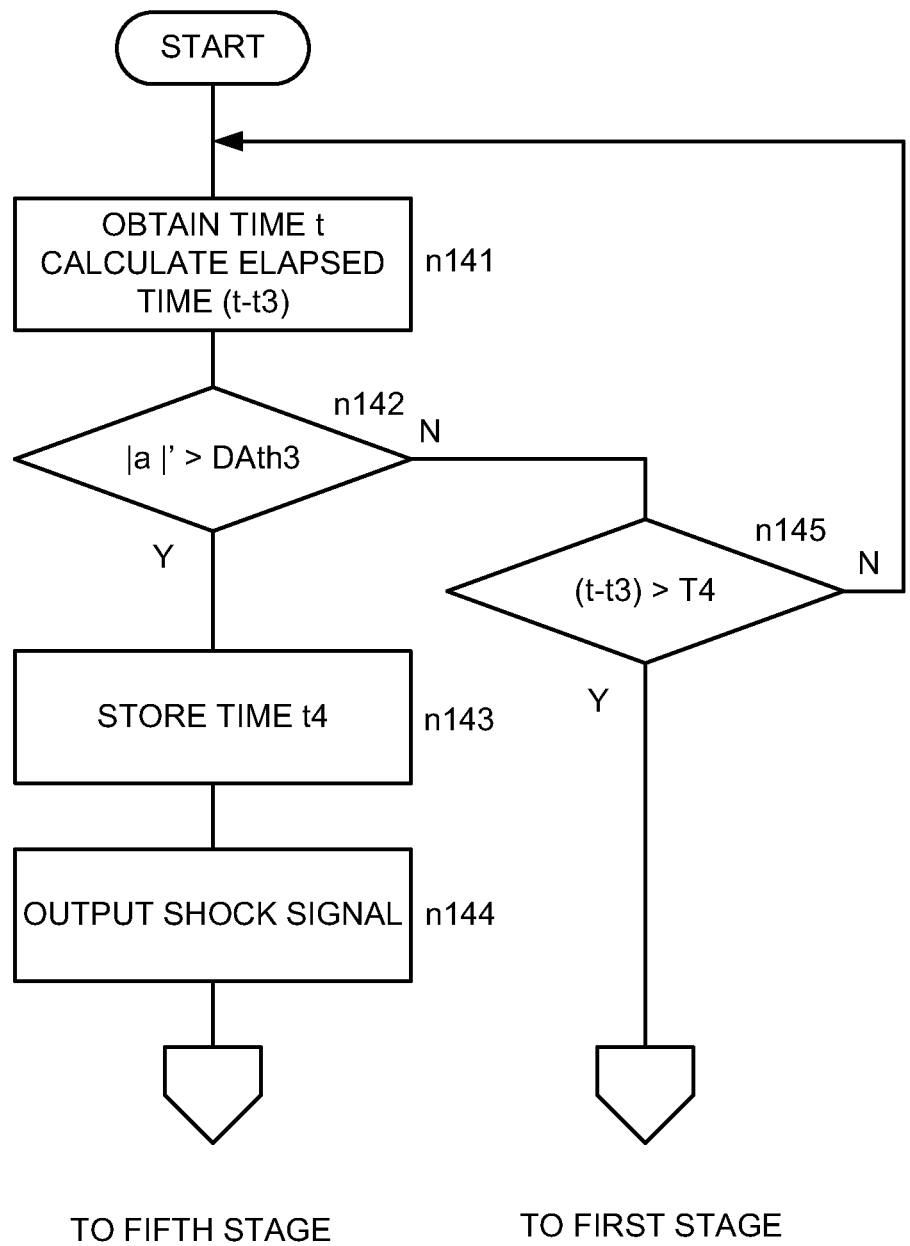
FIG. 17 is a flowchart showing an exemplary process in the fourth stage.

FIG. 17 is a flowchart showing processes in the fourth stage. First, the current time t is obtained, and the time (t−t3) that has elapsed since the movement to the third stage is calculated (n141). Then, whether the differential value |a|' of the absolute value of the acceleration exceeds the threshold DAth3 is determined. If the differential value exceeds the threshold, it is considered that a large shock has occurred due to a landing, and the then time t4 is stored and a shock signal is outputted. The process returns to the first stage (n142→n143→n144).

Even if the differential value |a|' of the absolute value of the acceleration does not exceed the threshold DAth3, it is considered that a shock has been avoided, provided that the elapsed time (t−t3) exceeds the prescribed time T4. The process returns to the first stage (n145→first stage).

Figure 18:
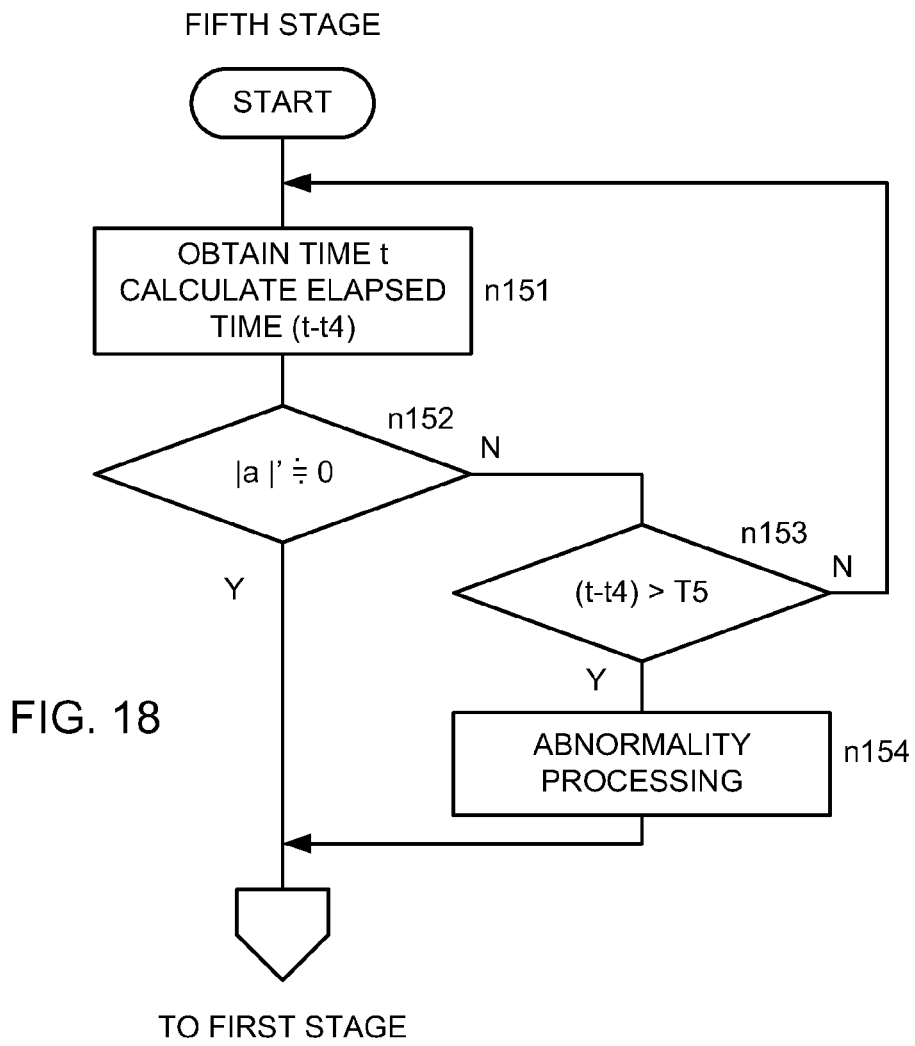
FIG. 18 is a flowchart showing an exemplary process in the fifth stage.

FIG. 18 is a flowchart showing processes in the fifth stage. First, the current time t is obtained, and the time (t−t4) that has elapsed since the movement to the fifth stage is calculated (n151). Then, if the differential value |a|' of the absolute value of the acceleration has become approximately 0, the process returns to the first stage, which is a steady state (n151→n152→first stage). If the differential value |a|' of the absolute value of the acceleration does not become approximately 0 even after the elapsed time (t−t4) has elapsed for the predetermined time T5, for example, an abnormality process considering that the fall detection device has been put into an abnormal state due to a shock is performed (n153→n154).

In the first and second exemplary embodiments, there have been shown the examples where the absolute value of the difference between the acceleration ao at a steady time and the acceleration a at a fall determination time is defined as the evaluation value A. For example, if the accelerations in the above-mentioned three axis directions are represented by ($a_{x0}$, $a_{y0}$, $a_{z0}$) and accelerations at the fall determination time are represented by ($a_x$, $a_y$, $a_z$), this is represented by the following equation:

$$A=\sqrt{\{(a_x-a_{x0})^2+(a_y-a_{y0})^2+(a_z-a_{z0})^2\}}.$$

It is preferable to obtain the above-mentioned evaluation value on the basis of an evaluation function, by which the evaluation value is increased as the difference between the acceleration at a steady time and the acceleration at the fall determination time is increased. For example, the evaluation value may be obtained by the following equations:

$$A=(a_x-a_{x0})^2+(a_y-a_{y0})^2+(a_z-a_{z0})^2, \text{ and}$$

$$A=|a_x-a_{x0}|+|a_y-a_{y0}|+|a_z-a_{z0}|.$$

Figure 19:
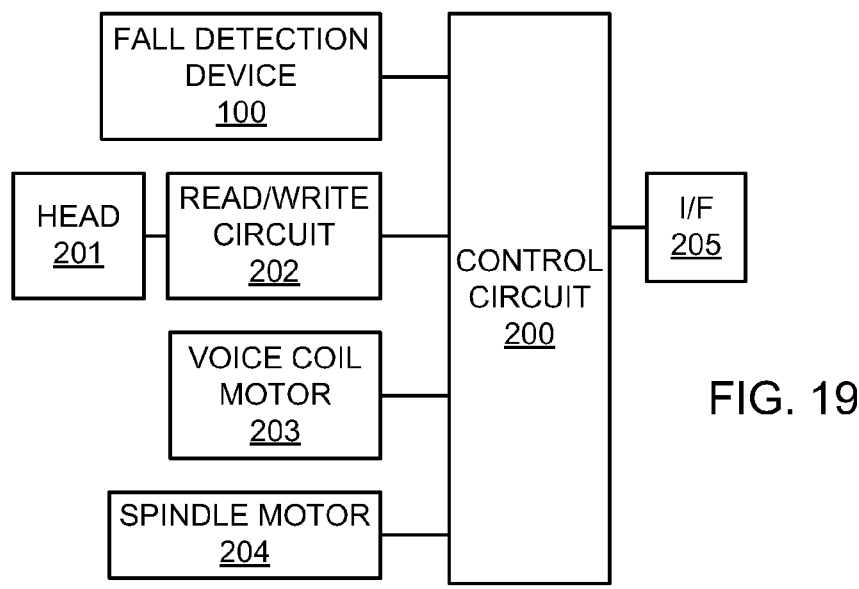
FIG. 19 is a block diagram showing a configuration of a magnetic disk drive according to an exemplary embodiment.

FIG. 19 is a block diagram showing a configuration of a magnetic disk drive such as a hard disk drive apparatus according to an exemplary third embodiment. A read/write circuit 202 reads data written into a track on a magnetic disk or writes data thereinto using a head 201. A control circuit 200 controls the read or write of data via the read/write circuit 202, and communicates this read/write data with a host apparatus via an interface 205. Also, the control circuit 200 controls a spindle motor 204 and a voice coil motor 203. Also, the control circuit 200 reads a fall detection signal sent from the fall detection device 100 and evacuates the head 201 to an evacuation area by controlling the voice coil motor 203 when the magnetic disk drive is placed in a fall state. Thus, for example, when a portable apparatus including the hard disk drive falls, the head is evacuated from an area of the magnetic disk to an evacuation area before the portable apparatus collides with the floor or ground. As a result, damage due to the touch of the head 201 on the recording surface of the magnetic disk is prevented.

Figure 20:
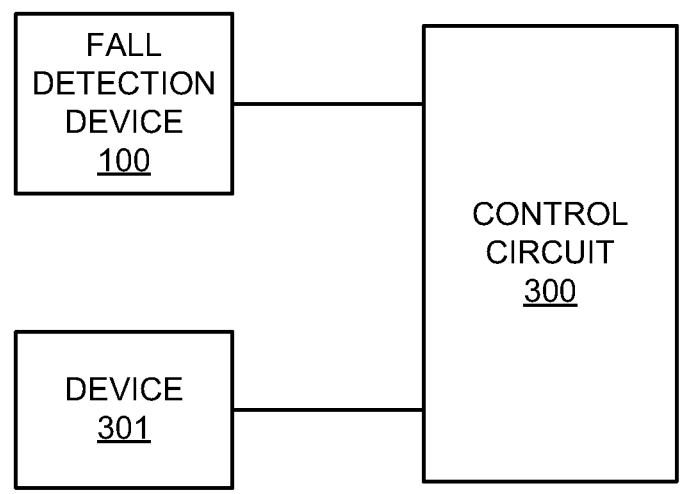
FIG. 20 is a block diagram showing a configuration of a portable electronic apparatus according to an exemplary embodiment.

FIG. 20 is a block diagram showing a configuration of a portable electronic apparatus including a hard disk drive apparatus, such as a notebook personal computer or a music/ video reproduction apparatus according to a fourth exemplary embodiment. The configuration of the fall detection device 100 is as described in the first or second embodiment. A device 301 is a device that must be protected from a shock due to collision caused when a fall occurs and is also a device that can undergo a countermeasure process for that purpose. For example, the device 301 is a hard disk drive apparatus. A control circuit 300 controls the device 301 on the basis of a signal outputted from the fall detection device 100. For example, if the control circuit 300 receives a fall warning signal (fall start signal) from the fall detection device 100, it performs a preliminary first-stage control on the device 301 in preparation for a shock to be given when a fall occurs. Also, if the control circuit 300 receives a signal indicating a fall-in-progress state (fall-in-progress signal), it performs a second-stage control on the device 301 in preparation for a shock to be given when a fall occurs.

Although a limited number of embodiments are described herein, one of ordinary skill in the art will readily recognize that there could be variations to any of these embodiments and those variations would be within the scope of the appended claims. Thus, it will be apparent to those skilled in the art that various changes and modifications can be made to the fall detection device, magnetic disk drive, and portable electronic apparatus described herein without departing from the scope of the appended claims and their equivalents.

The invention claimed is:

1. A fall detection device configured to detect a fall on the basis of a signal outputted from an acceleration sensor, the fall detection device comprising:

acceleration detection means that detects accelerations in three orthogonal axis directions; and fall start determination means that determines a steady time and accelerations in the three axis directions at the steady time by performing monitoring of an acceleration detected by the acceleration detection means, obtains an evaluation value with respect to the accelerations in the three axis directions detected by the acceleration detection means on the basis of an evaluation function, by which an evaluation value is increased as a difference increases between the acceleration at the determined steady time and an acceleration at a fall determination time in each of the three axis directions, and determines the start of a fall on the basis of whether the evaluation value exceeds a first predetermined threshold, wherein the steady time is a time just before a time when the absolute value of a differential value of an acceleration detected by the acceleration detection means exceeds a second predetermined threshold, and the fall determination time is a time just after a time when the absolute value of a differential value of an acceleration detected by the acceleration detection means falls below a third predetermined threshold.

2. The fall detection device according to claim 1, wherein if a value of the evaluation function is represented by A, the accelerations in the three axis directions at the steady time are represented by $(a_{x0}, a_{y0}, a_{z0})$ and the accelerations at the fall determination time are represented by $(a_x, a_y, a_z)$, relations among the A, the $(a_{x0}, a_{y0}, a_{z0})$, and the $(a_x, a_y, a_z)$ are represented by $A=\sqrt{\{(a_x-a_{x0})^2+(a_y-a_{y0})^2+(a_z-a_{z0})^2\}}$.

3. The fall detection device according to claim 1, wherein if a value of the evaluation function is represented by A, the accelerations in the three axis directions at the steady time are represented by $(a_{x0}, a_{y0}, a_{z0})$ and the accelerations at the fall determination time are represented by $(a_x, a_y, a_z)$, relations among the A, the $(a_{x0}, a_{y0}, a_{z0})$, and the $(a_x, a_y, a_z)$ are represented by $A=(a_x-a_{x0})^2+(a_y-a_{y0})^2+(a_z-a_{z0})^2$.

4. The fall detection device according to claim 1, wherein if a value of the evaluation function is represented by A, the accelerations in the three axis directions at the steady time are represented by $(a_{x0}, a_{y0}, a_{z0})$ and the accelerations at the fall determination time are represented by $(a_x, a_y, a_z)$, relations among the A, the $(a_{x0}, a_{y0}, a_{z0})$, and the $(a_x, a_y, a_z)$ are represented by $A=|a_x-a_{x0}|+|a_y-a_{y0}|+|a_z-a_{z0}|$.

5. The fall detection device according to claim 1, further comprising:

fall-in-progress detection means that detects whether the fall detection device is placed in a fall-in-progress state, the fall-in-progress state being a state in which a low-gravity state continues for a predetermined time or more, the low-gravity state being a state in which an absolute value of the acceleration falls below a fourth predetermined threshold within a predetermined time or falls within a predetermined range lower than a steady state after the fall start determination means considers that the fall detection device has been put into a fall start state.

6. A magnetic disk drive comprising:

the fall detection device according to claim 5;

a head that records data into a magnetic disk or reads data from the magnetic disk; and head evacuation means that evacuates the head to an evacuation area when the fall detection device detects the fall-in-progress state.

7. A portable electronic apparatus including the fall detection device according to claim 5 and a device that is allowed to undergo a shock-proof process, the portable electronic apparatus comprising:

shock-proof process means that performs the shock-proof process on the device when the fall detection device detects the fall-in-progress state.

8. The fall detection device according to claim 1, further comprising:

fall-in-progress detection means that detects whether the fall detection device is placed in a fall-in-progress state, the fall-in-progress state being a state in which a low-gravity state continues for a predetermined time or more, the low-gravity state being a state in which a differential value of an absolute value of the acceleration exceeds a fifth predetermined threshold within a predetermined time or falls within a predetermined range near 0 after the fall start determination means considers that the fall detection device has been put into a fall start state.

9. A magnetic disk drive comprising:

the fall detection device according to claim 8;

a head that records data into a magnetic disk or reads data from the magnetic disk; and head evacuation means that evacuates the head to an evacuation area when the fall detection device detects the fall-in-progress state.

10. A portable electronic apparatus including the fall detection device according to claim 8 and a device that is allowed to undergo a shock-proof process, the portable electronic apparatus comprising:

shock-proof process means that performs the shock-proof process on the device when the fall detection device detects the fall-in-progress state.

11. The fall detection device according to claim 1, further comprising:

fall-in-progress detection means that detects whether the fall detection device is placed in a fall-in-progress state, the fall-in-progress state being a state in which a low-gravity state continues for a predetermined time or more, the low-gravity state being a state in which an absolute value of a differential value of the acceleration falls below a sixth predetermined threshold within a predetermined time or falls within a predetermined range near 0 after the fall start determination means considers that the fall detection device has been put into a fall start state.

12. A magnetic disk drive comprising:
the fall detection device according to claim 11;
a head that records data into a magnetic disk or reads data from the magnetic disk; and
head evacuation means that evacuates the head to an evacuation area when the fall detection device detects the fall-in-progress state.

13. A portable electronic apparatus including the fall detection device according to claim 11 and a device that is allowed to undergo a shock-proof process, the portable electronic apparatus comprising:
shock-proof process means that performs the shock-proof process on the device when the fall detection device detects the fall-in-progress state.

14. A magnetic disk drive comprising:
the fall detection device according to claim 1;
a head that records data into a magnetic disk or reads data from the magnetic disk; and
head evacuation means that evacuates the head to an evacuation area when the fall detection device detects the fall start state.

15. A portable electronic apparatus including the fall detection device according to claim 1 and a device that is allowed to undergo a shock-proof process, the portable electronic apparatus comprising:
shock-proof process means that performs the shock-proof process on the device when the fall detection device detects the fall start state.

16. The fall detection device according to claim 1, wherein the fall start determination means determines the fall determination time by performing first and second monitoring of an acceleration detected by the acceleration detection; and the first monitoring and the second monitoring are sequentially performed.

17. The fall detection device according to claim 1, wherein the fall start determination means determines the steady time and the accelerations in the three axis directions at the steady time by determining whether or not the absolute value of a differential value of the acceleration exceeds the second predetermined threshold.

* * * * *